United States Patent
Alabaster et al.

(10) Patent No.: US 11,642,304 B2
(45) Date of Patent: May 9, 2023

(54) DIMETHYLSILOXANE-ALKYLENE OXIDE COPOLYMERS

(71) Applicant: CORNELIUS GROUP PLC, Bishop's Stortford (GB)

(72) Inventors: Thomas Guy Alabaster, Sudbury (GB); Hannah Ruth Beasley-Suffolk, Saffron Walden (GB); John Mark Bilney, Solihull (GB); Ella-Louise Ceraulo, Stevenage (GB); John Ing Chuan Daly, Hexhan (GB); Ian Stuart Pearce, Hexhan (GB); Elizabeth Joan Smith, Saffron Walden (GB); Robert Liam Smith, Nottingham (GB); Christos Angeletakis, Bear (DE); Yingfa Li, Bury Sr Edmund (GB)

(73) Assignee: CORNELIUS GROUP PLC, Bishop's Stortford (GB)

( * ) Notice: Subject to any disclaimer, the term of this patent is extended or adjusted under 35 U.S.C. 154(b) by 116 days.

(21) Appl. No.: 17/270,387

(22) PCT Filed: Jul. 25, 2019

(86) PCT No.: PCT/EP2019/070053
§ 371 (c)(1),
(2) Date: Feb. 22, 2021

(87) PCT Pub. No.: WO2020/021016
PCT Pub. Date: Jan. 30, 2020

(65) Prior Publication Data
US 2021/0186851 A1 Jun. 24, 2021

(30) Foreign Application Priority Data
Jul. 26, 2018 (GB) ...................... 1812188

(51) Int. Cl.
| | | |
|---|---|---|
| C08G 77/46 | (2006.01) | |
| A61Q 19/00 | (2006.01) | |
| C08G 65/336 | (2006.01) | |
| C08L 83/12 | (2006.01) | |
| A61K 8/90 | (2006.01) | |
| A61K 8/20 | (2006.01) | |
| A61K 8/25 | (2006.01) | |
| A61K 8/86 | (2006.01) | |
| A61K 8/891 | (2006.01) | |

(52) U.S. Cl.
CPC ............. *A61K 8/90* (2013.01); *A61K 8/20* (2013.01); *A61K 8/25* (2013.01); *A61K 8/86* (2013.01); *A61K 8/891* (2013.01); *A61Q 19/00* (2013.01); *A61K 2800/10* (2013.01); *A61K 2800/42* (2013.01); *A61K 2800/591* (2013.01)

(58) Field of Classification Search
None
See application file for complete search history.

(56) References Cited

U.S. PATENT DOCUMENTS

| | | | |
|---|---|---|---|
| 6,827,928 B2 | 12/2004 | Caes et al. | |
| 2013/0315650 A1* | 11/2013 | Cassin | A45D 40/262 401/268 |

FOREIGN PATENT DOCUMENTS

| | | | |
|---|---|---|---|
| CN | 105457074 A | 4/2016 | |
| JP | 2005-154736 * | 6/2005 | .............. A61K 8/90 |
| WO | WO 2020/021016 A1 | 1/2020 | |

OTHER PUBLICATIONS

Galin et al., Structural and thermodynamic study of dimethylsiloxane-ehtylene oxide PDMS-PEO-PDMS triblock copolymers, Macromolecules, vol. 14, No. 3, pp. 677-683, 1981.
International Preliminary Report On Patentability dated Jan. 26, 2021 for PCT/EP2019/070053 in 6 pgs.
International Search Report and Written Opinion dated Oct. 9, 2019 for PCT/EP2019/070053 in 7 pgs.
Isaacman, et al., Stealth Polymeric Vesicles via Metal-free Click Coupling, Biomacromolecules, vol. 14, No. 9, pp. 2996-3000, 2013.

* cited by examiner

*Primary Examiner* — Brian Gulledge
(74) *Attorney, Agent, or Firm* — Knobbe, Martens, Olson & Bear LLP

(57) ABSTRACT

Copolymers are formed of monomers of poly(dimethylsiloxane) and poly(alkylene oxide) of the following formula: $A_x\text{-XCH}_2\text{CH}_2\text{—}[B_yC_z]_n\text{—X-}A_x$. In the formula, each X independently represents a $\text{—CH}_2\text{—}$ group or an oxygen atom, A represents a polydimethylsiloxane derivative, B represents a polyethylene glycol unit, C represents a polypropylene glycol unit, x and n independently represent an integer from 1 to 150, and y and z independently represent an integer from 0 to 150. The copolymers can be used as emulsifiers in personal care compositions.

16 Claims, No Drawings

DIMETHYLSILOXANE-ALKYLENE OXIDE COPOLYMERS

PRIORITY AND CROSS REFERENCE TO RELATED APPLICATIONS

This application is the U.S. National Phase Application under 35 U.S.C. § 371 of International Application No. PCT/EP2019/070053, filed Jul. 25, 2019, designating the U.S. and published in English as WO 2020/021016 A1 on Jan. 30, 2020, which claims the benefit of Great Britain Application No. GB 1812188.9, filed Jul. 26, 2018. Any and all applications for which a foreign or a domestic priority is claimed is/are identified in the Application Data Sheet filed herewith and is/are hereby incorporated by reference in their entireties under 37 C.F.R. § 1.57.

FIELD

The invention relates to linear copolymers formed of monomers of poly(dimethylsiloxane) and poly(alkylene oxide), and their use as surfactants in personal care applications.

BACKGROUND

Owing to their unique properties such as water repulsion, interfacial activity and thermal stability etc., siloxanes are used in numerous industrial applications. These include the stabilization of polyurethane foams, and their use as emulsifiers in release coatings and in a variety of pharmaceutical/cosmeceutical applications and many others.

SUMMARY

The invention is set out in accordance with the appended claims. The invention provides for a polydimethylsiloxane-poly(alkyleneoxide) copolymer according to formula 1:

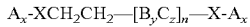

$$A_x\text{-}XCH_2CH_2\text{-}[B_yC_z]_n\text{-}X\text{-}A_x \qquad \text{formula 1}$$

wherein:
each X independently represents a —CH$_2$— group or an oxygen atom;
A represents a polydimethylsiloxane derivative;
B represents a polyethylene glycol unit;
C represents a polypropylene glycol unit;
x and n independently represent an integer from 1 to 150;
y and z independently represent an integer from 0 to 150; and
when y is 0, z is at least 1 and when z is 0, y is at least 1.

DETAILED DESCRIPTION

Silicone polymers have been known since 1880, however they did not become a major ingredient in the personal care industry until the 1990s. The designation "silicone polymers" covers a variety of silicon-based materials that are characterized by molecules or polymers that contain Si—O—Si bonds. Silicone polymers actually represent a whole range of materials ranging from simple silicon-based molecules (e.g., silanes) to "straight" polydimethyl siloxane polymers (of varying molecular weight) to linear and cyclic variations of these; to "organosilicone" copolymers of different chemistries (like "T" configurations or "ABA" type polymers); to cross linked variations of silicon-based materials which vary in the degree of cross-linking to generate yet another class of gelled "silicone polymers" of varying degrees of rheological behaviour and applications in the personal care and cosmetic industries.

There are a few key unusual functional attributes that make silicone a "must have" in a personal care formulation. These include: better surface tension reduction than that obtained with organic surfactants and, at much lower concentrations; as well as the capability of the forming associative films upon dry-down. Further, in view of the presence of the silicone moiety, these materials have expanded emulsification properties beyond those of organic surfactants. They also have foaming ability in both aqueous and nonaqueous environments, the capability to disperse pigments, and an ability to generate a desirable, unusual sensory/aesthetic silky feel.

The majority of silicone polymers employed in personal care compositions are of the ABA type polymers, comprising the coupling of a hydrophilic A-block, poly(ethylene glycol) (PEG), with a highly hydrophobic poly(dimethylsiloxane) (PDMS) B-block, to form well-defined amphiphilic ABA triblock copolymer.

"Stealth Polymeric Vesicles via Metal-free Click Coupling" to Isaacman, M. J. et al in Biomacromolecules (2013), Vol. 14 (9), pp. 2996-3000, discloses hydrophilic poly(oxazoline) (PMOXA) or poly(ethyleneglycol) (PEG) A-blocks which are coupled with a hydrophobic poly(siloxane) B-block to provide triblock copolymers capable of self-assembling into vesicular nanostructures.

"Structural and Thermodynamic Study of Dimethylsiloxane-Ethylene Oxide PDMS-PEO-PDMS Triblock Copolymers" to Malin et al. in Macromolcules (1981), Vol. 14, pp. 677-683 discloses a linear triblock PDMS-PEO-PDMS copolymer synthesized by hydrosilylation polycondensation wherein the molecular weights of the PEO block range from Mw=6,000-10,000, and the molecular weights of the PDMS block range from Mw=1,000-5,000.

U.S. Pat. No. 6,827,928 discloses a transfer-free composition comprising (a) at least one of a di-block, tri-block, multi-block and/or radial block copolymer and optionally (b) a film former or a mixture of film formers. Cosmetic and pharmaceutical compositions of the invention result in a film with very good retention, good transfer resistant properties, and which does not migrate over time.

A well-recognised problem with personal care compositions employing PEG/silicone AB- or ABA-type polymers relates to one of the unique properties of silicone fluids, in that they are insoluble in both water and oil. Since oil and water are two of the most common ingredients in cosmetic formulations, how they interact with the silicone polymers to produce personal care compositions is a significant key to formulation performance, stability and overall skin-feel to consumers. While there are many examples of ABA, AB alternating and comb structures already in use there is a need for further variants to provide one or more of enhancing the formulation flexibility by providing alternative materials, flexibility in design and manufacture of personal care compositions, improved processing of the final formulation as well as a simplification of the formulation used, giving rise to improved performance.

Copolymers of the present invention may act as emulsifiers in their own right, and may be incorporated into a range of personal care compositions to provide a unique touch/feel sensation to a user, without requiring a further or secondary co-emulsifier. Copolymers of the present invention have also been shown to demonstrate improved stability, in a simplified liquid person care formulation, over corresponding ABA, AB alternating and comb structures currently available.

Preferably copolymers of the invention are those in which x is in the range from 1 to 100. Highly preferred copolymers of the invention are those in which x is in the range from 5 to 30.

Preferably copolymers of the invention are those in which n is in the range from 1 to 100. Highly preferred copolymers of the invention are those in which n is in the range from 5 to 30.

Preferably copolymers of the invention are those in which y is in the range from 0 to 100. Highly preferred copolymers of the invention are those in which y is in the range from 6 to 40, such as when z=0.

Preferably copolymers of the invention are those in which z is in the range from 0 to 100. Highly preferred copolymers of the invention are those in which z is in the range from 5 to 10, such as when y=0.

Preferably copolymers of the invention are those in which y+z is in the range from 5 to 100. Highly preferred copolymers of the invention are those in which y+z is in the range from 11 to 40.

Preferably copolymers of the invention are those in which the polydimethylsiloxane unit $A_x$ is represented by formula 2:

$$R_1Si(CH_3)_2-[OSi(CH_3)_2]_x-$$ formula 2 wherein:

each group $R_1$ is independently a $C_1$-$C_6$ alkyl chain, preferably $C_1$; and x is as provided above in formula 1.

Preferably copolymers of the invention are those in which x is in the range selected from 5-30 and n is in the range selected from 5 to 40.

In the present invention the ratio of x to n, may be 1:0.1-7, preferably 1:0.4-2.4 and most preferably 1:0.2-1.5.

In the present invention y or z is 0, more preferably the ratio y:z=0.9 to 1.1, preferably 1.0.

In the present invention X is preferably 0.

Preferably copolymers of the invention are those in which x is in the range selected from 5-30, y is in the range selected from 6-40 and z=0. The skilled person will be aware that such so-formed copolymers do not comprise any polypropylene glycol units, and non-limiting examples of such copolymers include:

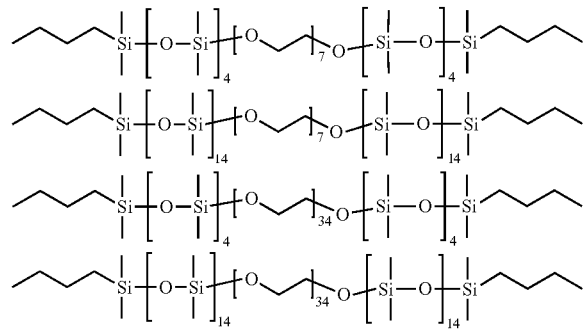

designated as PDMS5-PEG7, PDMS15-PEG7, PDMS5-PEG34 and PDMS14-PEG34 respectively, in accordance with the respective number of PDMS (A) and PEG (B) groups according to formula 1. For completeness, in each of these non-limiting examples, it is noted that when the polydimethylsiloxane unit $A_x$ is represented by formula 2 as provided above, group $R_1$ comprises a butyl chain, X is an oxygen atom and z is 0.

The skilled person will appreciate that copolymers of the invention may be block or random copolymers. Preferably copolymers of the invention are those in which the copolymer is a block copolymer. Further preferred block copolymers according to the invention are those of the type including, but not limited to, A-B-A, A-C-A, A-B-C-B-A, A-C-B-C-A or A-B-C-A wherein A, B and C are as defined for formula 1 above. Highly preferred copolymers of the present invention comprise an ABA (PDMS-PEG-PDMS) tri-block co-polymer structure.

Preferably copolymers of the invention are those in which the copolymer is a random copolymer. Random co-block polymers according to the invention can be formed when n is at least 2, and one of y or z is independently 0. A non-limiting example would be the random co-block polymer illustrated by A-[B-B-B-B-B-C]-[B-B]-A, wherein n=2, A, B and C are as defined in formula 1 above, the integer values (y and z) of B and C in the first n group being 5 and 1 respectively, and the integer values (y and z) of B and C in the second n group being 1 and 0 respectively.

While there are many examples of ABA, AB alternating and comb structures already in use, copolymers according to the present invention have a BAB tri-block co-polymer structure and have been surprisingly found to act as emulsifiers in their own right in personal care compositions, without the need for a co-emulsifier. This allows for flexibility in design and manufacture of personal care compositions, improved processing of the final formulation as well as a simplification of the formulation used, giving rise to improved performance.

Preferably copolymers of the invention are those having a viscosity in the range from 30 mPas to 1000 mPas. This makes them easier to incorporate into end use compositions, such as cosmetics.

Preferably copolymers of the invention are those having a molecular weight, in the range from 500 to 15,000. Highly preferred copolymers of the invention are those in which having a molecular weight, in the range from 1,000 to 13,000, more preferably 1,500 to 12,000.

Preferably copolymers of the invention are those having a polydispersity, Pa, in the range from 1.2 to 3.5.

Except where stated otherwise, the following definitions apply throughout the present specification and claims. These definitions apply regardless of whether a term is used by itself or in combination with other terms. For example, the definition of "alkyl" applies not only to alkyl groups per se, but also to the alkyl portions of alkoxy, alkylamino, alkylthio or alkylcarbonyl groups etc. Furthermore, all ranges described for a chemical group, for example "from 1 to 13 carbon atoms" or "C1-C6 alkyl" include all combinations and sub-combinations of ranges and specific numbers of carbon atoms therein.

In relation to the invention, the skilled person will appreciate that "alkyl" means a straight chain or branched chain aliphatic hydrocarbon group having from 1 to 20 carbon atoms in the chain. Preferred alkyl groups have from 1 to 12 carbon atoms in the chain. More preferred alkyl groups have from 1 to 6 carbon atoms in the chain. "Lower alkyl" means an alkyl group having about 1 to about 6 carbon atoms in the chain which may be straight or branched. Examples of suitable alkyl groups include methyl, ethyl, n-propyl, iso-propyl, sec-butyl, n-butyl, and t-butyl.

The invention also provides two methods of making a polydimethylsilicone-polyalkylene oxide copolymer, wherein the first method comprises reacting a polysiloxane precursor with polyalkylene oxide in the presence of a borane-based catalyst. The process is shown below for reference with regards the production of a PDMS-PEG copolymer comprising n and m units of the respective monomers, as illustrated.

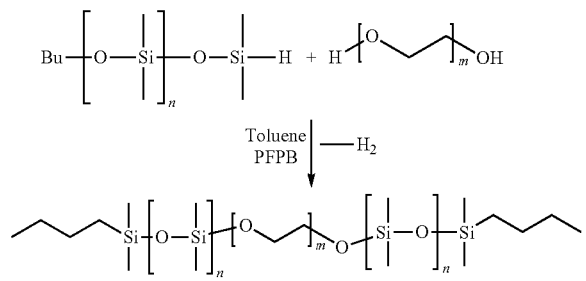

(PFPB=tris(pentafluorophenyl) borane)

The second method comprises reacting a polysiloxane precursor with polyalkylene oxide in the presence of a platinum-based catalyst. The process is shown below for reference with regards the production of a PDMS-PEG copolymer comprising n and m units of the respective monomers, as illustrated.

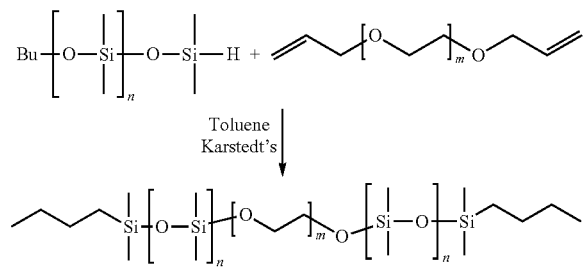

Karstedt's=Platinum-Divinyltetramethyldisiloxane Complex

The invention also provides two methods of making a polysiloxane precursor. The first comprises the reaction of hexamethylcyclotrisiloxane with butyl lithium and dimethylchlorosilane to produce an asymmetric silicone hydride. The process is shown below for reference with regards the production of a polysiloxane comprising n units of the monomers, as illustrated.

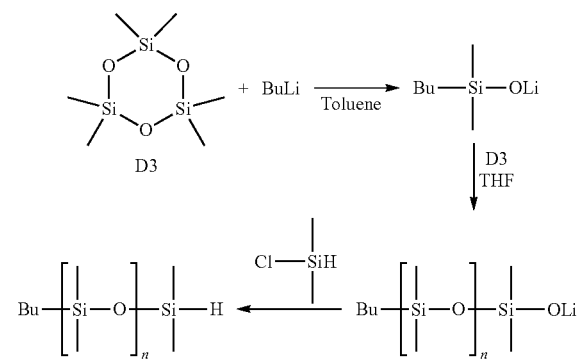

The second method comprises reacting pentemethyldisiloxane with octamethylcyclotetrasiloxane in the presence of an acidic catalyst to produce an asymmetric silicone hydride. It also produces symmetric silicones, hydride-terminated and trimethyl terminated. The process is shown below for reference with regards the production of a polysiloxane comprising n units of the monomers, as illustrated.

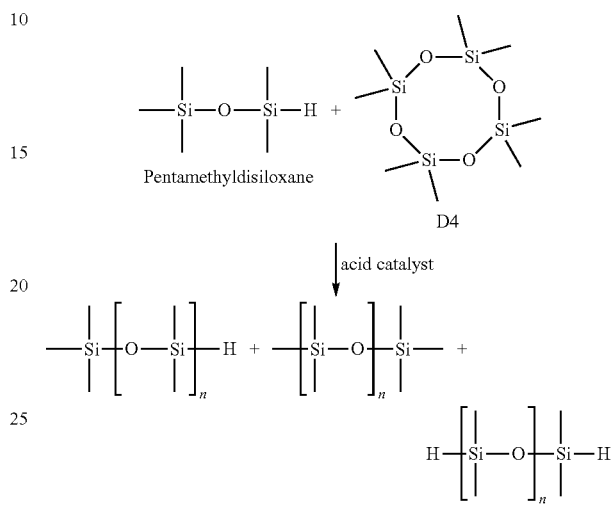

The invention also provides for use of a polydimethylsilicone-polyalkylene oxide copolymer in a personal care composition. Preferably the polydimethylsilicone-polyalkylene oxide copolymer acts as an emulsifier in such compositions and further preferably the copolymer is present in such compositions in amounts of less than 25 wt. % of the composition, preferably less than 20 wt. %, more preferably less than 15 wt. % and further preferably less than 10 wt. % of the composition. Highly preferably are personal care compositions comprising emulsifiers from 0.1 to 5 wt. % of the composition.

The properties of a representative personal care formulation were evaluated using a base composition of a liquid skin cream (i.e. without colorant or perfume) comprising 70-80% DI water, 0.2-1% salt, 10-26% dimethicone, 2-4% bentone pre-gel and 2-5% active emulsifier, all by weight. This was used to test the emulsifiers performance and allow for comparison, wherein a suitable bentone pre-gel is from the Bentone range of Elementis® specialities, such as Bentone 27. A suitable salt is sodium chloride. The active emulsifier is a nonionic surfactant.

The benefits of the polymer of the invention in the formulation (using the middle of above composition ranges) are:
- Acts as an emulsifier to form stable emulsions between water and dimethicone
- Works in a simple formulation (no need for co-emulsifiers),
- novel architecture could lead to novel textures for formulators,
- possible to get 'cushioning' effect without use of elastomers
- possible to get quick breaking emulsions that release water
- reduced manufacturing time as 'fast' homogenisation is possible Preferably the personal care composition comprising a copolymer as described above may further comprise one or more selected from the group consisting of an anionic surfactant, a cationic surfactant, a non-ionic co-surfactant, an amphoteric surfactant, or a semipolar surfactant.

Preferably the personal care composition comprising a copolymer as described above may further comprise a powder or a colorant selected from the group consisting of one or more of an inorganic pigment powder, an organic pigment powder, and a resin powder, having an average diameter in a range of 1 nm to 20 µm.

Preferably the personal care composition comprising a copolymer as described above may be a skin care product, a cosmetic product for hair, an anti-perspirant product, a makeup product, or an ultraviolet light blocking product. Most preferably a liquid skin care composition as the polymers of the present invention provide and enhanced feel to the user when applying to the skin.

Preferably the personal care composition comprising a copolymer as described above may be a liquid, cream, solid, paste, gel, powder or mousse. A liquid is preferred as the polymers of the present invention provide a shear thinning composition which has sufficient viscosity not to drip but can be readily spread on the skin.

Furthermore, the polydimethylsilicone-polyalkylene copolymers according to the present invention may function as a non-ionic surfactant and thus can reduce formulation complexity from addition of a further surfactant, such as the readily wet the skin when a composition comparing the polymer of the invention is spread on the skin. Therefore, there are the benefits of improved compounding stability and stability over time of these copolymers in personal care compositions.

The following detailed examples illustrate methods of making some of the compounds of general formula 1 as described above. These examples are illustrative only and are not intended to limit the scope of the invention. The reagents and starting materials are readily available to those skilled in the art.

Example 1

A 5 litre, round bottom flask equipped with stirrer bar, condenser and dropping funnel was oven dried and then cooled under a stream of nitrogen. Hexamethylcyclohexasiloxane (41 g) and toluene (70 ml) were introduced, then butyllithium (2.5M in hexanes, 200 ml) added dropwise under nitrogen, taking care to keep the reaction temperature below 40° C. After addition, the mixture was stirred at room temperature for 1 hour. The temperature was then increased to 40° C. and a solution of hexamethylcyclohexasiloxane (1040 g) in THF (2 litres) was added over the course of 2 hours. After addition, the mixture was stirred at 40° C. for 1 hour, before being reduced to room temperature. Dimethylchlorosilane (57 g) was added dropwise taking care to keep the reaction temperature below 35° C., the mixture was then left to stir at room temperature overnight with no nitrogen. Toluene (500 ml) and hexane (500 ml) were added and the reaction washed with de-mineralised water (3×2 litres) and brine (1×1 litre). Low boilers were removed at 100° C. under reduced pressure to give the final product B-PDMS30-H (1100 g). GC was used to determine if the low boilers had been removed, and the final product was analysed by GPC.

Analogous procedures were used to produce B-PDMS15-H and B-PDMS5-H by varying the amount of hexamethylcyclohexasiloxane in the second addition.

Example 2

Pentamethyldisiloxane (200 g), octamethylcyclotetrasiloxane (2240 g) and methanesulfonic acid (36 g) were combined in a 3 litre round bottom flask and stirred at 60° C. for 24 hours. The mixture was then cooled to room temperature and sodium bicarbonate (400 g) was slowly added before being stirred for 2 hours. The mixture was filtered. Volatiles were removed at 120° C. under reduced pressure to give the final product SiH-PDMS30 eq (1.913 g). GC was used to determine if the low boilers had been removed, and the final product was analysed by GPC.

Analogous procedures were used to produce SiH-PDMS5 eq, SiH-PDMS15 eq and SiH-PDMS100 eq by varying the amount of octamethylcyclotetrasiloxane.

Example 3

PEG divinyl ether, Mn 2200 (5 g) and toluene (100 ml) were placed in a 250 ml round bottom flask equipped with stirrer bar and Dean & Stark trap with condenser. The mixture was heated at 130° C. for 4 hours in which time 0.5 ml of water was collected. The temperature was reduced to 110° C. The Dean & Stark trap was removed, and the flask equipped with condenser, thermometer, dropping funnel and nitrogen sparge. Karstedt's catalyst (2% solution in xlyenes, 1 ml) was introduced and SiH-PDMS30 eq (89 g) added dropwise. The reaction was continued for 30 minutes after the addition was complete and IR used to confirm the absence of the SiH band. The temperature was reduced to 50° C. and activated charcoal (10 g) stirred in the mixture for 1 hour before being removed by filtration. Low boilers were removed at 70° C. under reduced pressure to give the final product PDMS30 eq-PEGS-Pt (630 g). GC was used to determine if the low boilers had been removed, and the final product was analysed by GPC and viscometry.

Example 4

PEG300 (42.5 g) and toluene (400 ml) were placed in a 1 litre round bottom flask equipped with stirrer bar and Dean & Stark trap with condenser. The mixture was heated at 120° C. for 4 hours in which time 5 ml of water was collected. The temperature was reduced to 80° C. The Dean & Stark trap was removed, and the flask equipped with condenser, thermometer, dropping funnel and nitrogen sparge. Tris(pentafluorophenyl) borane (1.65 g) was introduced and SiH-PDMS30 eq (630 g) added dropwise. The addition rate was controlled to keep the temperature below 90° C. and the foaming under control. The reaction was continued for 30 minutes after the addition was complete and IR used to confirm the absence of the SiH band. The temperature was reduced to 50° C. and basic alumina (50 g) stirred in the mixture for 1 hour before being removed by filtration. Low boilers were removed at 70° C. under reduced pressure to give the final product PDMS30 eq-PEG7 (630 g). GC was used to determine if the low boilers had been removed, and the final product was analysed by GPC and viscometry (for liquid products only).

Analogous procedures were used to produce all final products (except PDMS30 eq-PEGS-Pt) by combining the various PDMS and PEG/PPG chain lengths in a 2:1 ratio.

Results

A number of copolymers according to the invention were produced and tested, the results of such experiments and physical parameters being shown in the table below.

TABLE 1

Physical parameters of selected copolymers of the invention.

| Emulsifier | Appearance | Mn by GPC | PD by GPC | Viscosity (mPas) | Viscosity Settings |
|---|---|---|---|---|---|
| PDMS30eq-PEG7 | Clear liquid | 3700 | 2.9 | 119.2 | RV_HA_HB Spindle 2, 50 rpm |
| PDMS5eq-PEG7 | Thin hazy liquid | 1000 | 2.3 | 64.6 | RV_HA_HB Spindle 1, 50 rpm |
| PDMS100eq-PEG150 | Soft Wax | 7200 | 1.7 | Solid | N/A |
| PDMS15-PEG34 | Thick white liquid | 1600 | 1.8 | Solid | N/A |
| PDMS5-PEG34 | Soft white wax | 900 | 1.9 | Solid | N/A |
| PDMS30eq-PEG34 | Stiff cloudy gel | 4200 | 3.0 | Solid | N/A |
| PDMS30-PEG7 | Clear liquid | 8100 | 1.3 | 117.6 | RV_HA_HB Spindle 1, 50 rpm |
| PDMS15-PEG7 | Hazy liquid | 1300 | 1.6 | 21.2* | ULA Spindle, 20 rpm |
| PDMS5-PEG7 | Thin clear yellow liquid | 600 | 1.6 | 38 | RV_HA_HB Spindle 1, 50 rpm |
| PDMS30eq-PPG7 | Hazy liquid | 2700 | 3.4 | 104 | RV_HA_HB Spindle 2, 50 rpm |
| PDMS30eq-PEG5-Pt | Dark liquid | 2900 | 2.9 | 97.4* | ULA Spindle, 5 rpm |
| PDMS30eq-(PEG75-PPG30-PEG75-Block) | Hard Wax | 25717 | 1.2 | Solid | N/A |
| PDMS30eq-(PEG25-PPG25-Random) | Thick hazy liquid/gel | 6800 | 3.4 | 91141 | Cone and Plate, 1 rpm |

An example formulation was prepared in accordance with Table 2 below. Other formulations were prepared in an analogous manner and summarised in Table 3 below.

TABLE 2

Preparation of example formulation.

| Phase A | Dimethicone 5CS | qs to 100% |
|---|---|---|
| | Bentone 38 10% Pregel | 2-4% |
| | Active Emulsifier | 2-5% |
| Phase B | DI water (preserved) | 70-80% |
| | Salt (MgSO4 or NaCl) | 0.2-1% |

Method: To Prepare 300 g Batch

Prepare Phase A: Disperse Bentone pregel into Dimethicone 5Cs with high shear mixer. Stir in emulsifier.

Prepare phase B: weigh water and stir in salt until dissolved.

Stirrer Method:

Place Silicone phase A under Heidolph RZR 2020 overhead stirrer with 3 blade 5 cm propeller impeller. Set speed to 300 rpm. Slowly pipette water phase over 15 mins into the vortex. Turn speed up to 1050-1300 rpm depending on viscosity of emulsion for 5 mins to emulsify and reduce droplet size.

Post Homogenised Method:

Prepare emulsion as per stirrer method then place under Silverson homogeniser for 2 mins.

Fast Homogenised Method:

Use Silverson L4R with 5 cm emulsor screen. Place phase B under homogeniser. Set to speed 2 (~1800 rpm). Pour water phase B into vortex slowly over 3 mins. Continue mixing for a further 2 mins.

All formulations cold mixed, except for those marked * which are solid. Processing was at 70° C.

Emulsions were classed as Si/W or W/Si depending on the behaviour of a droplet when dropped into a beaker of water. Si/W emulsions immediately dispersed into the water, whereas W/Si emulsions remained as an intact droplet.

Stability Testing:

All samples stored in 40° C. incubator oven for 12 weeks. Samples were stored in sealed plastic 50 g clear PET bottles. Samples assessed weekly. Emulsions were visually assessed for separation. A small sample was spread on the surface of a spatula to check for emulsion homogeneity, and any signs of water droplet coalescence. Samples showing visible water droplets or phase separation failed stability.

GPC Testing:

$CHCl_3$ GPC data was recorded on an Agilent Infinity II MDS instrument equipped with a differential refractive index (DRi) detector. The software was Agilent's Cirrus (V3.4.1). add-on to Chemstation. The system was equipped with a PLgel Mixed C column and a PLgel Mixed E column (300×7.5 mm), with a PLgel 5 μm guard column. The mobile phase was $CHCl_3$ and run at a flow rate of 1 ml min$^{-1}$ at 35° C. Agilent polystyrene standards were used to create third order calibrations from DRI data between 300,000 and 580 g mol$^{-1}$. To prepare the samples ~20 mg was added to a vial and 7 ml of $CHCl_3$ eluent added.

GC Testing:

Analysis was carried out on an HP5890 GC instrument using Agilent Chemstation software. The column was an RTX-5 GC Capillary Column and the detector an FID. The temperature ramp was: Initial at 60° C., hold 5 minutes, ramp at 20° C./min to 320° C., hold 17 minutes.

Viscosity Testing.

Emulsifier viscosities were measured at room temperature using a Brookfield RV-DV1. Spindles and speeds were varied as appropriate.

Viscosities for low volumes of emulsifiers below 100 mPas were measured at 25° C. using a Brookfield LV-DV1+ with ULA adapter and spindle.

Viscosities for low volumes of emulsifiers above 500 mPas were measured at 24° C. using a Brookfield DV2THB cone and plate using spindle CPA-42Z, and time stop of 60 s.

In this document emulsion sample viscosity is measured at room temperature using a Brookfield RV-DV1 at 10 rpm. Spindles RV/HA/HB2-6 were used as appropriate.

Texture Method:

A trained panel of 3 assessed approximately 0.2-0.3 ml of each emulsion on the inner forearm. Product was gently rubbed in for 30 seconds, in which time assessments were made on the heaviness, quick breaking and water droplet effect. Cushion was assessed at 60 seconds. The panel discussed and agreed the test results.

Heaviness—Perception of how rich feeling the emulsion was on application. Scale set from 1 to 5 where the richest feeling emulsions (1&2) were determined to be 5, setting the top of the scale.

Quick Breaking—The perception of how quickly the emulsion structure broke giving the sensation of rubbing a fluid onto the skin.

Water Droplet—If the emulsion formed droplets of water on the skin. 5=water droplets formed instantly as the emulsion was applied. Lower scores indicate that some water droplets formed during application. 1=no water droplets were perceived as the product was applied. Cushion—Perception of a silky after feel left on the skin. 5=a silky after feel easily perceptible, 1=no residue of the product could be felt.

Example formulations 1 to 5 below are comparison examples and do not fall within the scope of the invention. They are produced for comparison purposes only. Example formulations 6 to 28 all fall within the scope of the invention.

TABLE 3

|   | Emulsifier | Emulsifier % | Water phase % | Man. Method | Emulsion Type | Salt | Bentone % | Weeks Stable @ 40° C. | Viscosity (mPas) | Viscosity Settings | Texture Score 1 = low, 5 = high |
|---|---|---|---|---|---|---|---|---|---|---|---|
| 1 | Jeesilc EM90 (Cetyl PEG/PPG-10/1 Dimethicone) | 5 | 75 | Fast Homogenised | W/Si | MgSO4 0.2% | 0 | 8 | 55000 | Spin 6, 10 rpm | Heaviness: 5 Quick breaking: 1 Cushion: 3 Water Droplet: 1 |
| 2 | Jeesilc EM90 (Cetyl PEG/PPG-10/1 Dimethicone) | 5 | 73 | Fast Homogenised | W/Si | MgSO4 0.2% | 0.2 | 9 | 38000 | Spin 6, 10 rpm | Heaviness: 5 Quick breaking: 1 Cushion: 3 Water Droplet: 1 |
| 3 | Dow 5225C (PEG/PPG-18/18 Dimethicone) | 16 (2% active) | 80 | Stirrer | W/Si | NaCl 1% | 0 | 12+ | 16680 | Spin 5, 10 rpm | Heaviness: 4 Quick breaking: 1 Cushion: 3 Water Droplet: 1 |
| 4 | PEG-8 Dimethicone (Jeesilc DS-8) | 5 | 73 | Stirrer | W/Si | MgSO4 0.2% | 0.2 | 0 | N/A | N/A | N/A |
| 5 | PEG-8 Dimethicone (Jeesilc DS-8) | 5 | 73 | Fast Homogenised | W/Si | MgSO4 0.2% | 0.2 | 0 | N/A | N/A | N/A |
| 6 | PDMS30eq-PEG7 | 5 | 70 | Fast Homogenised | W/Si | MgSO4 0.2% | 0.4 | 12+ | 15540 | Spin 4, 10 rpm | Heaviness: 3 Quick breaking: 3 Cushion: 3 Water Droplet: 1 |
| 7 | PDMS30eq-PEG7 | 5 | 80 | Stirrer | W/Si | MgSO4 0.2% | 0.2 | 12+ | 21440 | Spin 5, 10 rpm | Heaviness: 1 Quick breaking: 5 Cushion: 3 Water Droplet: 5 |
| 8 | PDMS30eq-PEG7 | 5 | 85 | Stirrer | W/Si | MgSO4 0.2% | 0.2 | 12+ | 29080 | Spin 5, 10 rpm | Heaviness: 1 Quick breaking: 5 Cushion: 2 Water Droplet: 5 |
| 9 | PDMS5eq-PEG7 | 5 | 70 | Stirrer | W/Si | MgSO4 0.2% | 0.2 | 1 | 1250 | Spin 2, 10 rpm | Heaviness: 2 Quick breaking: 3 Cushion: 4 Water Droplet: 1 |
| 10 | PDMS5eq-PEG7 | 5 | 73 | Stirrer | W/Si | MgSO4 0.2% | 0.2 | 12+ | 7460 | Spin 4, 10 rpm | Heaviness: 3 Quick breaking: 2 Cushion: 4 Water Droplet: 1 |
| 11 | PDMS5eq-PEG7 | 5 | 73 | Post Homogenised | W/Si | MgSO4 0.2% | 0.2 | 12+ | 9480 | RV_HA_HB Spindle 3, 10 rpm | Heaviness: 3 Quick breaking: 3 Cushion: 3 Water Droplet: 1 |

TABLE 3-continued

| | Emulsifier | Emulsifier % | Water phase % | Man. Method | Emulsion Type | Salt | Bentone % | Weeks Stable @ 40° C. | Viscosity (mPas) | Viscosity Settings | Texture Score 1 = low, 5 = high |
|---|---|---|---|---|---|---|---|---|---|---|---|
| 12 | *PDMS100 eq-PEG150 Trial 2 | 5 | 73 | Stirrer | W/Si | MgSO4 0.2% | 0.2 | 4 | 1900 | RV_HA_HB Spindle 4, 20 rpm | Heaviness: 1 Quick breaking: 5 Cushion: 1 Water Droplet: 5 |
| 14 | PDMS15-PEG34 | 5 | 73 | Stirrer | Si/w | MgSO4 0.2% | 0.2 | 12+ | 23 | RV_HA_HB Spindle 1, 100 rpm | Heaviness: 1 Quick breaking: 4 Cushion: 5 Water Droplet: 1 |
| 15 | *PDMS5-PEG34 | 5 | 73 | Stirrer | Si/w | MgSO4 0.2% | 0.2 | 1 | 15.6 | RV_HA_HB Spindle 1, 50 rpm | Heaviness: 1 Quick breaking: 4 Cushion: 3 Water Droplet: 1 |
| 16 | *PDMS30eq-PEG34 | 5 | 73 | Stirrer | W | MgSO4 0.2% | 0.2 | 0 | 25 | RV_HA_HB Spindle 1, 100 rpm | N/A |
| 17 | PDMS30-PEG7 | 5 | 80 | Stirrer | W/Si | MgSO4 0.2% | 0.2 | 10 | 21240 | RV_HA_HB Spindle 5, 10 rpm | Heaviness: 2 Quick breaking: 3 Cushion: 4 Water Droplet: 1 |
| 18 | PDMS30-PEG7 | 5 | 80 | Post Homogenised | W/Si | MgSO4 0.2% | 0.2 | 10 | 18220 | RV_HA_HB Spindle 4, 10 rpm | Heaviness: 3 Quick breaking: 3 Cushion: 4 Water Droplet: 1 |
| 19 | PDMS30-PEG7 | 2 | 80 | Stirrer | W/Si | MgSO4 0.2% | 0.2 | 12+ | 16440 | RV_HA_HB Spindle 5, 10 rpm | Heaviness: 3 Quick breaking: 2 Cushion: 4 Water Droplet: 1 |
| 20 | PDMS30-PEG7 | 2 | 80 | Post Homogenised | W/Si | MgSO4 0.2% | 0.2 | 12+ | 14420 | RV_HA_HB Spindle 4, 10 rpm | Heaviness: 2 Quick breaking: 5 Cushion: 2 Water Droplet: 3 |
| 21 | PDMS30-PEG7 | 5 | 80 | Fast Homogenised | W/Si | MgSO4 0.2% | 0.2 | 12+ | 32840 | RV_HA_HB Spindle 5, 10 rpm | Heaviness: 2 Quick breaking: 5 Cushion: 2 Water Droplet: 5 |
| 22 | PDMS15-PEG7 | 5 | 73 | Stirrer | W/Si | MgSO4 0.2% | 0.2 | 11 | 6020 | RV_HA_HB Spindle 4, 10 rpm | Heaviness: 2 Quick breaking: 4 Cushion: 2 Water Droplet: 1 |
| 23 | PDMS15-PEG7 | 5 | 73 | Post Homogenised | W/Si | MgSO4 0.2% | 0.2 | 12+ | 8240 | RV_HA_HB Spindle 4, 10 rpm | Heaviness: 2 Quick breaking: 5 Cushion: 2 Water Droplet: 1 |
| 24 | PDMS5-PEG7 | 5 | 73 | Stirrer | W/Si | MgSO4 0.2% | 0.2 | 8 | 4700 | RV_HA_HB Spindle 3, 10 rpm | Heaviness: 1 Quick breaking: 2 Cushion: 3 Water Droplet: 1 |
| 25 | PDMS5-PEG7 | 5 | 70 | Fast Homogenised | W/Si | MgSO4 0.2% | 0.2 | 4 | 6240 | RV_HA_HB Spindle 4, 10 rpm | Heaviness: 1 Quick breaking: 3 Cushion: 3 Water Droplet: 1 |
| 26 | PDMS30eq-PPG7 | 5 | 80 | Stirrer | W/Si | MgSO4 0.2% | 0.2 | 2+ | 12000 | RV_HA_HB Spindle 4, 10 rpm | Heaviness: 1 Quick breaking: 5 Cushion: 1 Water Droplet: 5 |
| 27 | PDMS30eq-PEG5-Pt | 5 | 80 | Stirrer | W/Si | MgSO4 0.2% | 0.2 | 2+ | 8100 | RV_HA_HB Spindle 3, 10 rpm | Heaviness: 2 Quick breaking: 4 Cushion: 2 Water Droplet: 5 |
| 28 | PDMS30eq-PEG5-Pt | 5 | 80 | Post Homogenisation | W/Si | MgSO4 0.2% | 0.2 | 1+ | 15980 | RV_HA_HB Spindle 4, 10 rpm | Heaviness: 2 Quick breaking: 4 Cushion: 2 Water Droplet: 5 |
| 29 | PDMS30eq-(PEG75-PPG30-PEG75-Block) | 5 | 80 | Stirrer | W/Si | MgSO4 0.2% | 0.2 | 0 | N/A | N/A | N/A |
| 30 | PDMS30eq-(PEG25-PPG25-Random) | 5 | 80 | Stirrer | Si/W | MgSO4 0.2% | 0.2 | 0 | N/A | N/A | N/A |

All percentage compositions herein are by weight unless otherwise specified. All methods herein are measured at 20° C., also termed 'room temperature' unless specified otherwise. Water used herein is de-mineralised water unless specified otherwise.

What is claimed is:

1. A polydimethylsiloxane-poly(alkyleneoxide) copolymer according to formula 1:

$$A_x\text{-}XCH_2CH_2\text{—}[B_yC_z]_n\text{—}X\text{-}A_x \qquad \text{formula 1}$$

wherein:
X represents an oxygen atom;
A represents a polydimethylsiloxane derivative;
B represents a polyethylene glycol unit;
C represents a polypropylene glycol unit;
x and n independently represent an integer from 1 to 150;
y is an integer from 1 to 150; and
z independently is an integer from 0 to 300; and
when y is 0, z is at least 1 and when z is 0, y is at least 1.

2. The copolymer according to claim 1, wherein x is in the range from 1 to 100 and not less than 2n and not more than 20n.

3. The copolymer according to claim 1, wherein n is in the range from 1 to 100.

4. The copolymer according to claim 1, wherein y is in the range from 0 to 100 and y+z is greater than 1.

5. The copolymer according to claim 1, wherein z is in the range from 0 to 100 and y+z is greater than 1.

6. The copolymer according to claim 1, wherein the polydimethylsiloxane unit $A_x$ is represented by formula 2:

$$R_1Si(CH_3)_2\text{—}[OSi(CH_3)_2]_x\text{—} \qquad \text{formula 2}$$

wherein:
each group $R_1$ is independently a C1-C6 alkyl chain; and
x is as defined for formula 1.

7. The copolymer according to claim 1, wherein x is in the range selected from 5-30 and n is in the range selected from 5 to 40.

8. The copolymer according to claim 1, wherein x is in the range selected from 5-30, y is in the range selected from 5-34 and z=0.

9. The copolymer according to claim 1, wherein the ratio of x to n is in the range 1:0.1 to 1:7.

10. The copolymer of claim 9, wherein the ratio of x to n is in the range 1:0.4 to 1:2.4.

11. The copolymer of claim 10, wherein the ratio of x to n is in the range 1:0.2 to 1:1.5.

12. The copolymer according to claim 1, wherein y or z is 0.

13. The copolymer according to claim 1, wherein the ratio y:z is in the range 0.9 to 1.1.

14. The copolymer according to claim 12, wherein the ratio y:z is 1.0.

15. The copolymer according to claim 1, having a molecular weight, Mn, in the range from 600 to 81,000.

16. A personal care composition comprising a polydimethylsilicone-polyalkylene oxide copolymer according to claim 1.

* * * * *